US011944752B2

(12) United States Patent
Baiko (10) Patent No.: US 11,944,752 B2
(45) Date of Patent: Apr. 2, 2024

(54) DIMPLED FLAP FOR A PATIENT INTERFACE DEVICE

(71) Applicant: KONINKLIJKE PHILIPS N.V., Eindhoven (NL)

(72) Inventor: Robert William Baiko, Monroeville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 495 days.

(21) Appl. No.: 17/113,382

(22) Filed: Dec. 7, 2020

(65) Prior Publication Data
US 2021/0187231 A1 Jun. 24, 2021

Related U.S. Application Data (60) Provisional application No. 62/951,454, filed on Dec. 20, 2019.

(51) Int. Cl.
*A61M 16/06* (2006.01)
*A61M 16/00* (2006.01)
*A61M 16/08* (2006.01)

(52) U.S. Cl.
CPC .... *A61M 16/0622* (2014.02); *A61M 16/0616* (2014.02); *A61M 16/0066* (2013.01); *A61M 16/0683* (2013.01); *A61M 16/0875* (2013.01)

(58) Field of Classification Search
CPC .............. A61M 16/06; A61M 16/0605; A61M 16/0611; A61M 16/0616; A61M 16/0622; A61M 16/0627; A61M 16/0683; A62B 18/02; A62B 18/025
See application file for complete search history.

(56) References Cited

U.S. PATENT DOCUMENTS

| | | | |
|---|---|---|---|
| 2,939,458 A | 6/1960 | Lundquist | |
| 7,302,951 B2 | 12/2007 | Castiglione et al. | |
| 9,375,545 B2 | 6/2016 | Darkin | |
| 9,717,871 B2 | 8/2017 | Baiko | |
| 9,907,924 B2 | 3/2018 | Eury | |
| 2006/0042629 A1* | 3/2006 | Geist | A61M 16/06 128/206.26 |
| 2008/0006277 A1 | 1/2008 | Worboys | |
| 2008/0230068 A1* | 9/2008 | Rudolph | A61M 16/0616 128/206.28 |
| 2010/0024811 A1* | 2/2010 | Henry | A61M 16/0622 128/202.16 |
| 2010/0065059 A1* | 3/2010 | Ho | A61M 16/0875 128/206.24 |
| 2011/0186051 A1* | 8/2011 | McAuley | A61M 16/06 128/206.24 |
| 2013/0146060 A1* | 6/2013 | Ho | A61M 16/0057 128/205.25 |
| 2014/0044905 A1* | 2/2014 | Nickol | A61M 16/06 264/571 |
| 2014/0326246 A1* | 11/2014 | Chodkowski | A61M 16/0622 128/206.24 |
| 2015/0013682 A1* | 1/2015 | Hendriks | A61M 16/0605 29/592 |

(Continued)

*Primary Examiner* — Joseph D. Boecker (74) *Attorney, Agent, or Firm* — Michael W. Haas (57) ABSTRACT

A cushion member for use in a patient interface device for delivering a flow of breathing gas to an airway of a patient includes a plurality of dimples defined in a portion of the cushion member.

17 Claims, 5 Drawing Sheets (56) References Cited

U.S. PATENT DOCUMENTS

| | | | |
|---|---|---|---|
| 2015/0040909 A1* | 2/2015 | Willard | A61M 16/0633 |
| | | | 128/205.25 |
| 2015/0047644 A1* | 2/2015 | Baiko | A61M 16/0622 |
| | | | 128/206.26 |
| 2016/0354572 A1* | 12/2016 | Lim | A61J 15/0003 |
| 2017/0368286 A1* | 12/2017 | Grashow | A61M 16/0616 |
| 2021/0128862 A1 | 5/2021 | Baiko | |

* cited by examiner

DIMPLED FLAP FOR A PATIENT INTERFACE DEVICE

CROSS-REFERENCE TO RELATED APPLICATIONS

This patent application claims the priority benefit under 35 U.S.C. § 119(e) of U.S. Provisional Application No. 62/951,454, filed on Dec. 20, 2019, the contents of which are herein incorporated by reference.

BACKGROUND OF THE INVENTION

1. Field of the Invention

The present invention relates to patient interface devices for use in providing a flow of breathing gas to the airway of a patient and, more particularly, to cushion members for use in such patient interface devices. The present invention also relates to systems for providing a flow of breathing gas to the airway of a patient that include such patient interface devices.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion member on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is connected to a gas delivery tube or conduit and interfaces the pressure support device with the airway of the patient, so that a flow of breathing gas can be delivered from the pressure/flow generating device to the airway of the patient.

Sealing cushions typically include sealing flaps that are intended to engage the face of the patient about one or more airways of the patient. Such engagement needs to provide a seal, but at the same time needs to accomplish such seal in as comfortable manner as possible. Current sealing flaps are limited by their shape and functional aspects. Thin flaps lack structural elements to support themselves and sustain minor forces, but allow for the flap to contain high strain with low force. Thick flaps contain structural elements to support themselves and loads, but the flaps strain little with applied load and often times will cause red marks. Engineers currently attack this problem with changing of durometer. However, changing durometer does not address the issue of thick flaps providing structure and thin flaps providing increased strain. Accordingly, there is room for improvement.

SUMMARY OF THE INVENTION

Embodiments of the present invention address shortcomings in the art by providing arrangements that provide both stretch and structure simultaneously. As one aspect of the present invention a cushion member for use in a patient interface device for delivering a flow of breathing gas to an airway of a patient is provided. The cushion member comprises a plurality of dimples defined in a portion of the cushion member.

The portion may comprise a sealing flap having a first outer surface that is structured to sealingly engage the patient at or about the airway of the patient, and an inner surface disposed on an opposite side of the sealing flap from the outer surface, wherein the dimples are defined in the inner surface.

The portion may comprise a support flap underlying a sealing flap of the cushion member.

The portion may comprise a wall structure of the cushion member.

The dimples may be positioned in a multi-dimensional array. The multi-dimensional array may comprise a 3-dimensional array.

The dimples may be defined in an interior portion of the cushion.

The dimples may be of different size. The dimples may be of the same shape. The dimples may be of different shapes.

As another aspect of the invention, a patient interface device for use in a system adapted to provide a flow of breathing gas to the airway of a patient is provided. The patient interface device comprises: a frame member; and a cushion member coupled to the frame member, wherein at least one of the frame member or the cushion member comprises a plurality of dimples defined in a portion thereof.

The cushion may comprise a sealing flap having: a first outer surface structured to sealingly engage the patient at or about the airway of the patient, and an inner surface disposed on an opposite side of the sealing flap from the outer surface, wherein the portion comprises the inner surface of the sealing flap.

The portion may comprise a support flap of the cushion member underlying a sealing flap of the cushion member.

The portion may comprise a wall structure of the cushion member.

As yet another aspect of the present invention, a system adapted to provide a flow of breathing gas to the airway of a patient is provided. The system comprises: a pressure generating device structured to produce the flow of breathing gas; a delivery conduit having a first end coupled to the pressure generating device and an opposite second end, the delivery conduit being structured to receive the flow of breathing gas from the pressure generating device at the first end and communicate the flow of breathing gas from the first end to the second end; and a patient interface device having a cushion member coupled to the second end of the delivery conduit, the cushion member being structured to sealingly engage about the airway of the patient and to communicate the flow of breathing gas from the second end of the delivery conduit to the airway of the patient, wherein the cushion member comprises a plurality of dimples defined in a portion thereof.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF EXEMPLARY EMBODIMENTS

As required, detailed embodiments of the present invention are disclosed herein; however, it is to be understood that the disclosed example embodiments described herein are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are coupled directly in contact with each other. As used herein, "fixedly coupled" or "fixed" means that two components are coupled so as to move as one while maintaining a constant orientation relative to each other.

As used herein, the statement that two or more parts or components "engage" one another shall mean that the parts exert a force against one another either directly or through one or more intermediate parts or components. As used herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
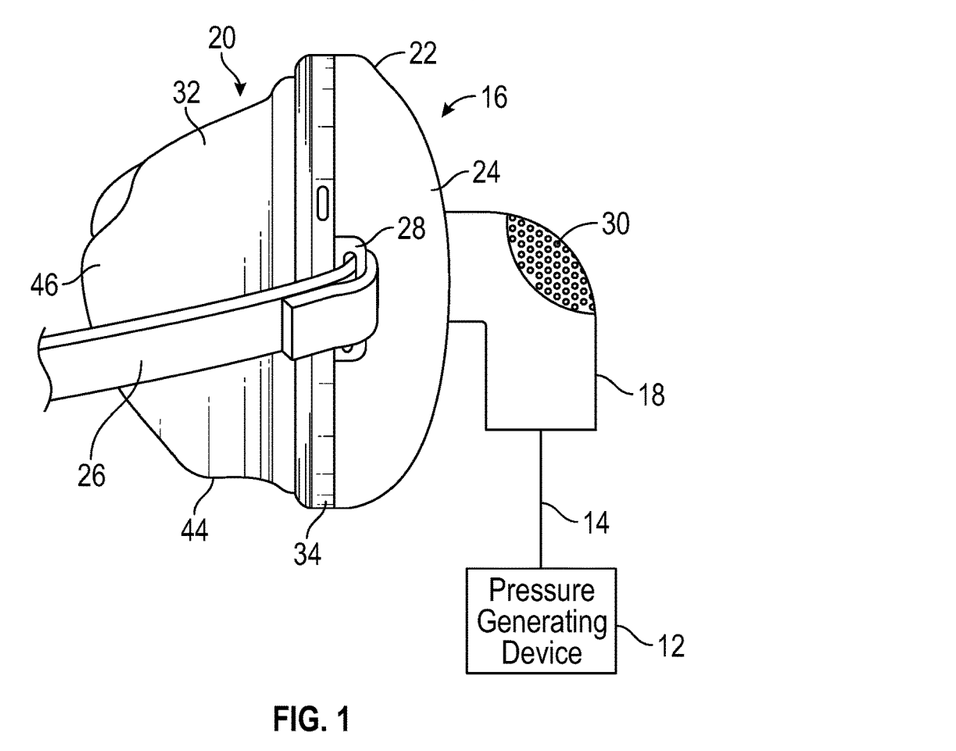
FIG. 1 is a schematic diagram of a system adapted to provide a regimen of respiratory therapy to a patient in accordance with one non-limiting example embodiment of the present invention.

A system 10 adapted to provide a regimen of respiratory therapy to a patient according to one exemplary embodiment of the present invention is generally shown in FIG. 1. System 10 includes a pressure generating device 12, a delivery conduit 14, and a patient interface device 16 including an elbow conduit 18. Pressure generating device 12 is structured to generate a flow of breathing gas and may include, without limitation, ventilators, constant pressure support devices (such as a continuous positive pressure device, or CPAP device), variable pressure device (e.g., BiPAP®, Bi-Flex®, or C-Flex™ devices manufactured and distributed by Philips Respironics of Murrysville, PA), and auto-titration pressure support devices. Delivery conduit 14 is structured to communicate the flow of breathing gas from pressure generating device 12 to patient interface device 16.

In the one example embodiment illustrated in FIG. 1, patient interface device 16 comprises a nasal mask structured to cover the nose of the patient, however, other types of patient interface devices, such as, without limitation, a nasal/oral mask that covers the patient's nose and mouth, or a full face mask that covers the patient's face, which facilitates the delivery of the flow of breathing gas to, and the removal of a flow of exhalation gas from, the airway of a patient may be used while remaining within the scope of the present invention. In the embodiment shown in FIG. 1, patient interface device 16 includes a cushion assembly 20 and a frame member 22 having a faceplate portion 24. Frame member 22 is made of a rigid or semi-rigid material, such as, without limitation, an injection molded thermoplastic or silicone. One or more straps 26 of a headgear component may be attached to faceplate portion 24 via attachment members 28 to secure patient interface device 16 to the patient's head. An opening in faceplate portion 24 to which elbow conduit 18 is coupled allows the flow of breathing gas from pressure generating device 12 to be communicated to an interior space defined by faceplate portion 24 and cushion assembly 20, and then, to the airway of a patient. The opening in faceplate portion 24 also allows the flow of exhalation gas (from the airway of such a patient) to be communicated to exhaust vent 30 provided in elbow conduit 18.

Figure 2:
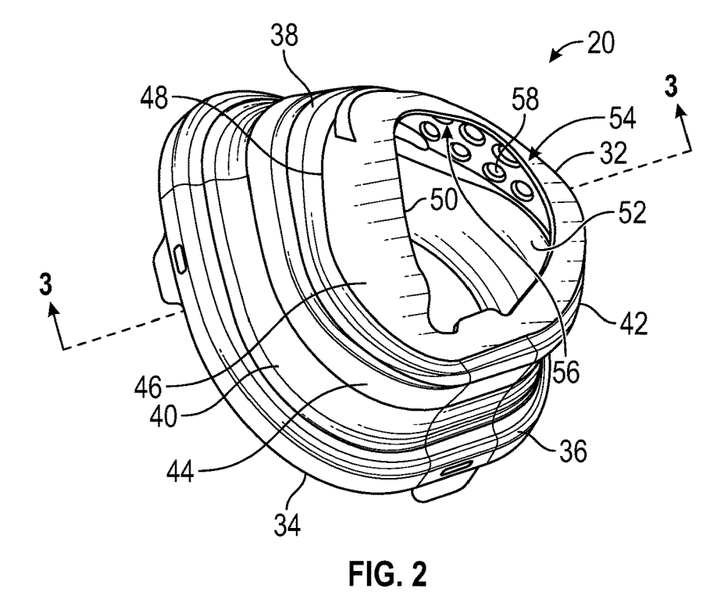
FIG. 2 is a side isometric view of a cushion assembly forming part of a patient interface device of FIG. 1.
Figure 3:
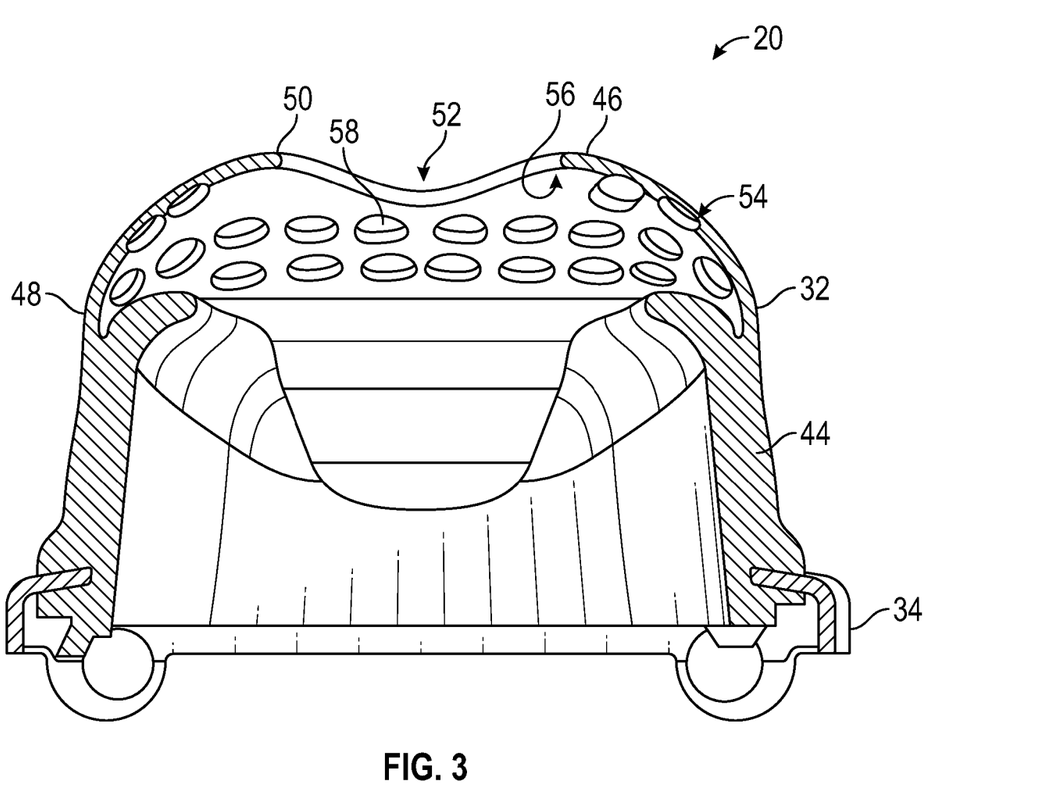
FIG. 3 is a sectional view of the cushion assembly of FIG. 2 taken along line 3-3 of FIG. 2.

Continuing to refer to FIG. 1 as well as FIGS. 2 and 3, cushion assembly 20 includes a cushion member 32 coupled to a support ring 34. Support ring 34 is made from a rigid or semi-rigid material, such as, without limitation, an injection molded thermoplastic or silicone, and facilitates secure fluid connection of cushion assembly 20 to frame member 22.

In the one example embodiment shown in FIGS. 1-3, cushion member 32 is defined from a unitary piece of soft, flexible, cushiony, elastomeric material, such as, without limitation, silicone or an appropriately soft thermoplastic elastomer, or any combination of such materials. It will be understood, however, that cushion member 32 does not need to be unitary within the scope of the present invention. Rather, cushion member 32, and the parts thereof, may be made of separate components (e.g., separate sealing flap and support portion) that are coupled to one another by suitable means. Also in the exemplary embodiment, cushion assembly 20 has a generally triangular shape including a bottom region 36, an apex region 38 located opposite bottom region 36, a first side region 40 and a second side region 42 located opposite first side region 40. As a result, both cushion member 32 and support ring 34 will have associated bottom, apex and first and second side regions.

Cushion member 32 includes an outer wall 44 comprising a support portion of cushion member 32 and a sealing flap 46 that extends inwardly from outer wall 44. As seen in FIGS. 2 and 3, sealing flap 46 overlies a smaller, thicker, support flap and includes a proximal end 48 coupled to the top edge of outer wall 44 and a distal end 50 opposite proximal end 48, wherein distal end 50 defines an opening 52 structured to receive the patient's nose. Sealing flap 46 thus extends in a direction that is generally transverse to a longitudinal axis of cushion assembly 20.

Continuing to refer to FIGS. 2 and 3, sealing flap 46 of cushion member 32 includes an outer surface 54 and an inner surface 56. Outer surface 54 is structured to sealingly engage the skin of a patient at or about an airway of the patient. Inner surface 56 is disposed on the opposite side of sealing flap 46 from outer surface 54 and as such generally faces away from the patient. Inner surface 56 includes a plurality of dimples 58 formed therein that are disposed in a multi-dimensional array. As used herein, the term "dimple" shall refer to a feature that is defined extending into an object from a surface of the object. In example embodiments of the present invention, such features are close-ended, hence, in such example embodiments grooves or channels do not constitute a "dimple" as such term is used herein. As discussed further below in conjunction with FIGS. 4-9, such arrangement of dimples 58 in sealing flap 46 provides for a sealing flap that both allows for stretch and provides structure, in contrast to conventional arrangements which generally provide for only one or the other. Further, such arrangement prevents bucking of sealing flap 46. The quantity of dimples may be varied depending on the particular embodiment of the present invention.

Referring now to FIGS. 4-9, function of a multi-dimensional dimpled arrangement 100, similar to that of sealing flap 46, in accordance with one example embodiment of the present invention will now be discussed. Dimpled arrangement 100 includes a flexible sheet 102 formed from a unitary piece of soft, flexible, cushiony, elastomeric material, such as, without limitation, silicone or an appropriately soft thermoplastic elastomer, or any combination of such materials. Sheet 102 has a thickness t, which in the one example embodiment shown in FIGS. 4-6 and 8 is 1 mm. It is to be appreciated, however, that such thickness t is given for example purposes only and that other thicknesses may be employed without varying from the scope of the present invention.

Figure 4:
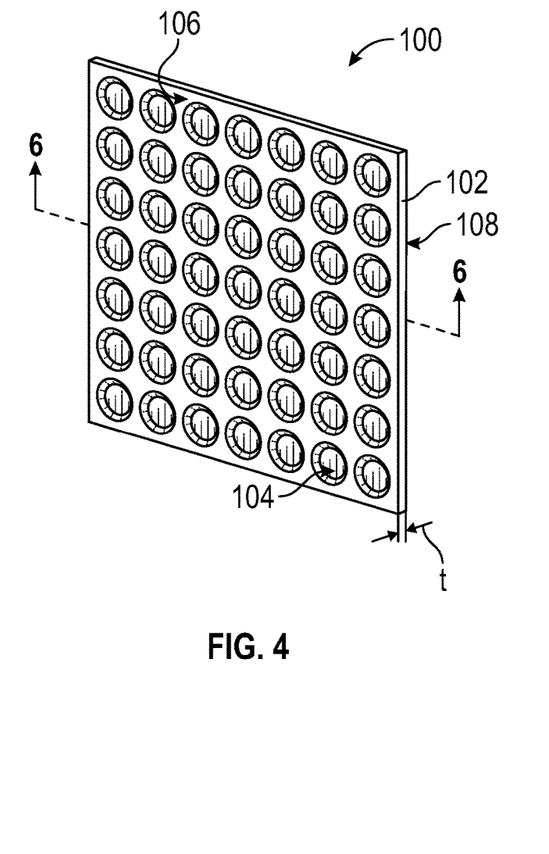
FIG. 4 is a perspective view of a dimpled portion of material in accordance with one example embodiment of the present invention.

Dimpled arrangement 100 further includes a plurality of dimples 104 formed in sheet 102. More particularly, each dimple 104 extends inward from a first surface 106 of sheet 102 toward a second surface 108 of sheet 102 opposite first surface 106 a depth d that is less than thickness t of sheet 102, resulting in sheet 102 having a reduced thickness $t_R$ at each dimple 104 equal to thickness t−depth d. In the one example embodiment shown in FIGS. 4-6 and 8, each dimple 104 has a depth d of 0.6 mm, thus resulting in a reduced thickness $t_R$ of 0.4 mm at each dimple 104. It is to be appreciated, however, that such depth d is provided for example purposes only and that other depths d may be employed without varying from the scope of the present invention. Although shown as being circular with tapered sides, it is to be appreciated that each dimple 104 may be of other size, shape, and/or have walls of different profile without varying from the scope of the present invention. For example, without limitation, dimples in the form of domes, countersinks, squares, and hexagons have been employed in example embodiments of the present invention. It is also to be appreciated that dimples 104 may be arranged in a fixed repeating pattern or array (such as shown in the example embodiment of FIGS. 4 and 5) or may be arranged in a varying pattern and/or be of varying size without varying from the scope of the present invention. It is further to be appreciated that the array of dimples 104 illustrated in FIG. 4 is an example of a 2-dimensional array as dimples 104 are spaced in 2 dimensions (i.e., are spaced into columns and rows). In contrast, if dimples 104 were further spaced in a third direction, e.g., if sheet 102 were formed as a curved sheet, dimples 104 would then be disposed in a 3-dimensional array. Dimples 58 of the example embodiment of FIGS. 1-3 are disposed in a 3-dimensional array.

Figure 5:
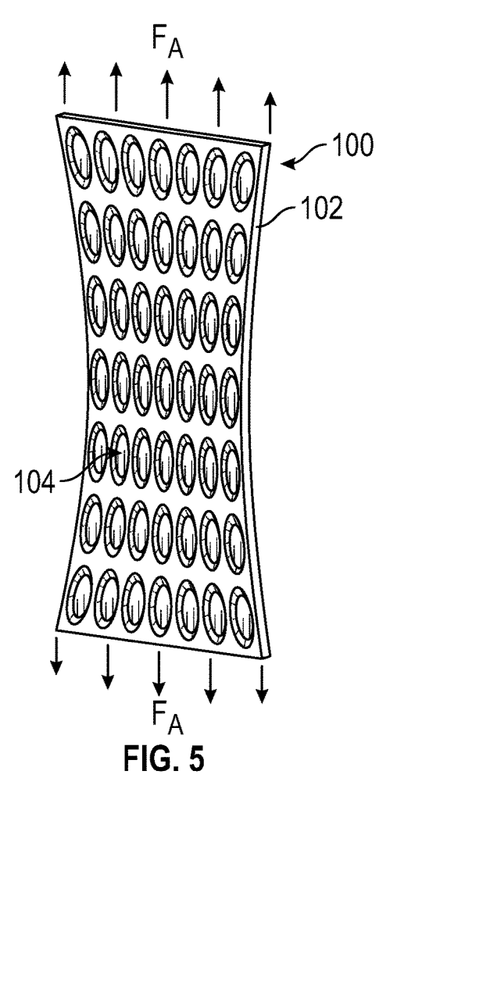
FIG. 5 is a perspective view of the dimpled portion of material of FIG. 4 shown with an axially applied loading.
Figure 6:
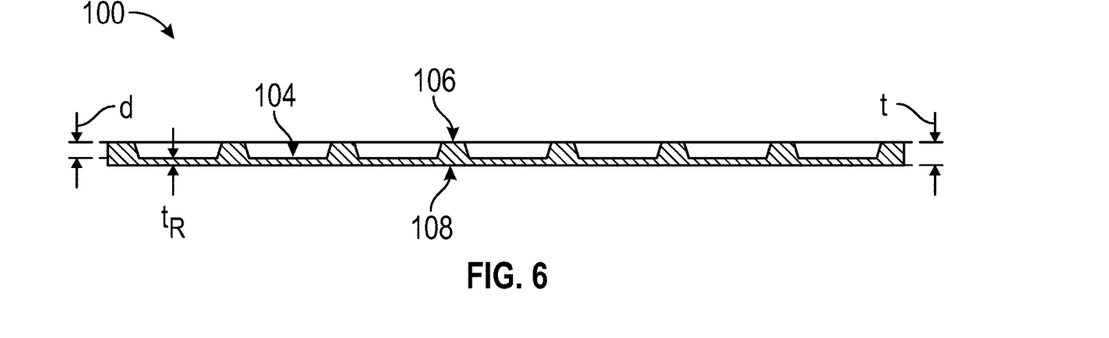
FIG. 6 is a sectional view of the dimpled portion of material of FIG. 4 taken along line 6-6 of FIG. 4.
Figure 7:
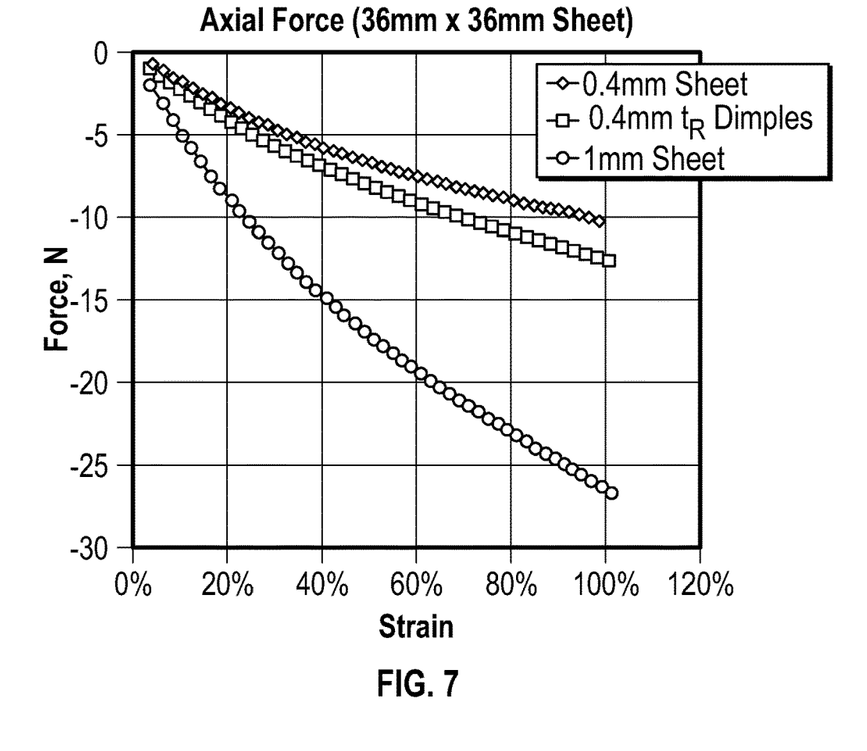
FIG. 7 is a graph showing a comparison of axial loading and resulting strain of a dimpled sheet in accordance with one example embodiment of the present invention compared with two non-dimpled sheets of different thicknesses.

Referring now to FIG. 7, a graphical comparison of sheet 102 loaded axially, such as by an axial force FA as shown in FIG. 5, along with regular (i.e., non-dimpled) sheets having a thickness t of 1 mm (i.e., the same thickness t as sheet 102) and 0.4 mm (i.e., the same thickness t as reduced thickness $t_R$ of each dimple 104 of sheet 102 loaded axially in the same manner as sheet 102. From such results it can be readily appreciated that sheet 104 (shown by the graph composed of squares) behaves similarly to the sheet having a thickness t of 0.4 (shown by the graph composed of solid dots), and not like the sheet having a thickness t of 1 mm. Hence, sheet 104 provides similar stretch to the sheet having the same thickness as the reduced thickness $t_R$ of dimples 104 and not that of the sheet having the same thickness t as sheet 104.

Figure 8:
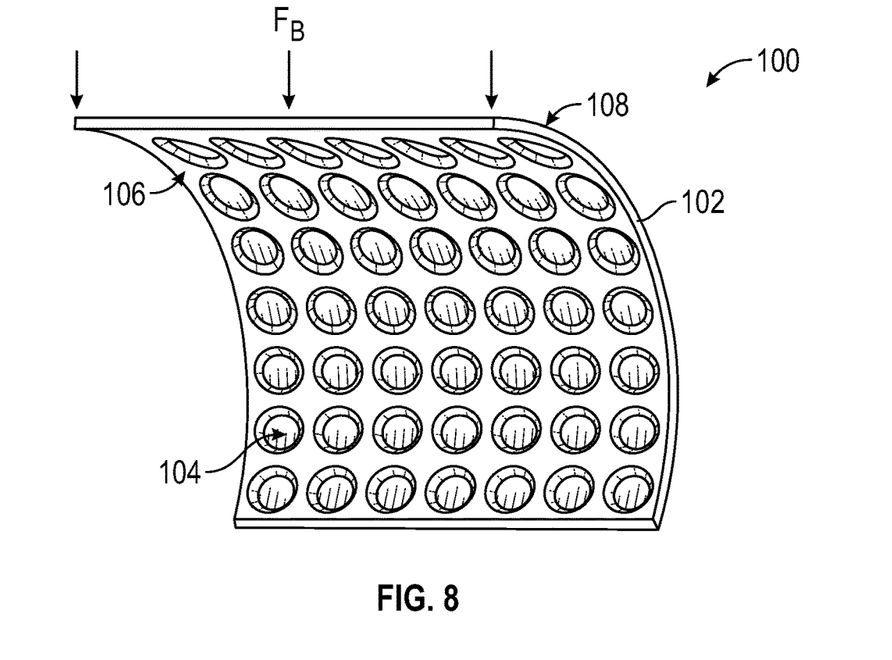
FIG. 8 is a perspective view of the dimpled portion of material of FIG. 4 shown with a bending load applied.
Figure 9:
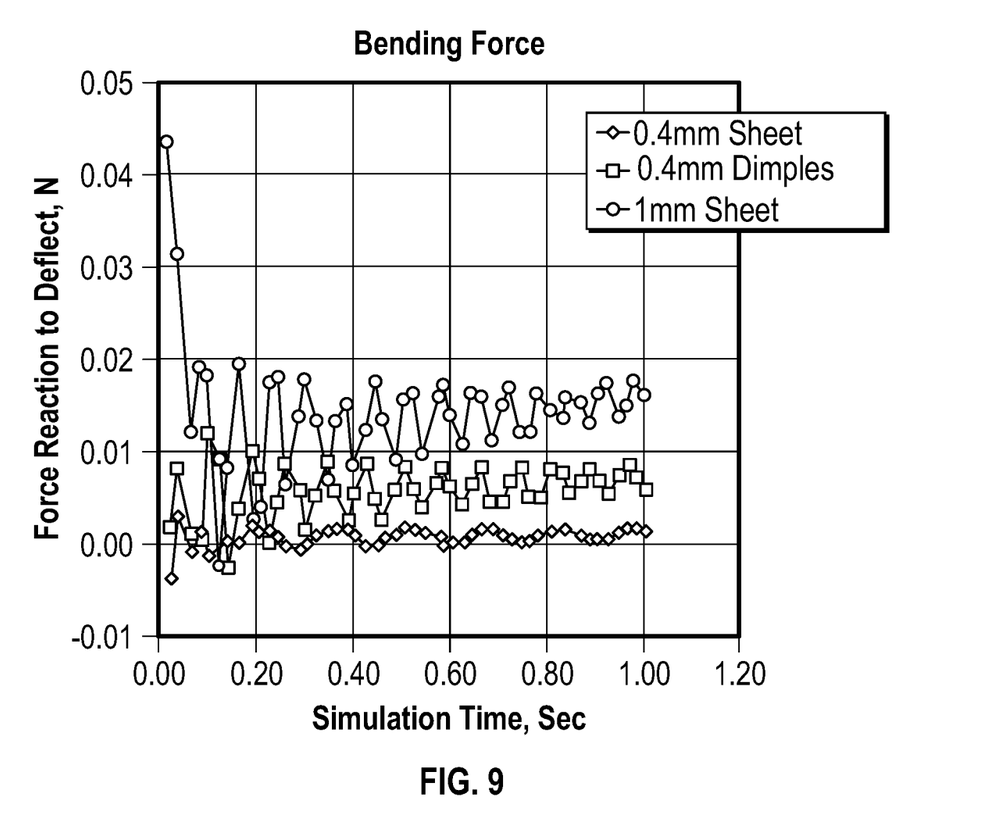
FIG. 9 is a graph showing a comparison of applied bending loads to a dimpled sheet in accordance with one example embodiment of the present invention compared with two non-dimpled sheets of different thicknesses.

Referring now to FIG. 9, a graphical comparison of sheet 102 loaded to induce bending, such as by a bending force FB as shown in FIG. 8, along with regular (i.e., non-dimpled) sheets having a thickness t of 1 mm (i.e., the same thickness t as sheet 102) and 0.4 mm (i.e., the same thickness t as reduced thickness $t_R$ of each dimple 104 of sheet 102 loaded to induce bending in the same manner as sheet 102. From such results it can be readily appreciated that sheet 104 (shown by the graph composed of squares) behaves generally midway between the sheet having a thickness t of 0.4 (shown by the graph composed of solid dots) and the sheet having a thickness t of 1 mm. Hence, sheet 104 provides structure roughly part way between the sheet having the same thickness as the reduced thickness $t_R$ of dimples 104 and the sheet having the same thickness t as sheet 104.

From the example results shown in FIGS. 7 and 9 it is thus to be appreciated that dimpled sheet 104 provide similar stretch as a much thinner sheet but at the same time provides greater structure than the thin sheet.

Although the one example embodiment shown in FIGS. 1-3 employs dimples in a sealing flap of a nasal mask, it is to be appreciated that similar arrangements of dimples may be employed other in other portions of a patient interface as well as other types of interfaces without varying from the scope of the present invention. For example, without limitation, arrangements of dimples may be employed in one or more of: support flaps of cushions, wall structures of cushions, faceplates, hosing, moldable headgear (e.g., without limitation, within a silicone frame of a DreamWear mask manufactured by Philips Respironics), and/or any other suitable location. Additionally, such dimpled portions may be formed in only selected areas or regions of such portions (e.g., without limitation, in a sealing flap only adjacent the corners of a mouth, at or about the apex near the bridge of a patient's nose, etc.). Such other types of patient interfaces in which arrangements of dimples may be employed include, for example, without limitation, full face masks, pillows masks, cradle masks, and total face masks (i.e., covering the eyes, mouth, and nose).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A cushion member for use in a patient interface device for delivering a flow of breathing gas to an airway of a patient, the cushion member comprising a sealing flap having:
   a plurality of dimples defined therein,
   wherein the sealing flap has a first thickness between the plurality of dimples,
   wherein the sealing flap has a second thickness at each dimple that is less than the first thickness, and
   wherein the plurality of dimples are arranged in a pattern such that the sealing flap has one or both of:
      a stretch property of a first reference flap having a uniform thickness of the second thickness; and/or
      a structural property of a second reference flap having a uniform thickness less than the first thickness and greater than the second thickness.

2. The cushion member of claim 1, wherein the sealing flap comprises:
   an outer surface structured to sealingly engage the patient at or about the airway of the patient, and
   an inner surface disposed on an opposite side of the sealing flap from the outer surface, and wherein the plurality of dimples are defined in the inner surface.

3. The cushion member of claim 1, wherein the dimples are positioned in a multi-dimensional array.

4. The cushion member of claim 3, wherein the multi-dimensional array comprises a 3-dimensional array.

5. The cushion member of claim 1, wherein the dimples are defined in an interior portion of the cushion member.

6. The cushion member of claim 1, wherein the dimples are of different size.

7. The cushion member of claim 1, wherein the dimples are of the same shape.

8. The cushion member of claim 1, wherein the dimples are of different shapes.

9. The cushion member of claim 1, wherein the dimples are arranged in a varying pattern.

10. The cushion member of claim 1, wherein the sealing flap has both of: the stretch property of the first reference flap having the uniform thickness of the second thickness; and the structural property of the second reference flap having the uniform thickness less than the first thickness and greater than the second thickness.

11. A patient interface device for use in a system adapted to provide a flow of breathing gas to the airway of a patient, the patient interface device comprising:
   a frame member; and
   a cushion member coupled to the frame member, the cushion member comprising a sealing flap having a plurality of dimples defined therein,
   wherein the sealing flap has a first thickness between the plurality of dimples,
   wherein the sealing flap has a second thickness at each dimple that is less than the first thickness, and wherein the plurality of dimples are arranged in a pattern such that the sealing flap has one or both of:
  a stretch property of a first reference flap having a uniform thickness of the second thickness; and/or
  a structural property of a second reference flap having a uniform thickness less than the first thickness and greater than the second thickness.

12. The patient interface device of claim 11, wherein the sealing flap comprises:
  an outer surface structured to sealingly engage the patient at or about the airway of the patient, and
  an inner surface disposed on an opposite side of the sealing flap from the outer surface, and wherein the portion comprises the inner surface of the sealing flap.

13. The patient interface device of claim 11, wherein the dimples are arranged in a varying pattern.

14. The patient interface of claim 11, wherein the sealing flap has both of: the stretch property of the first reference flap having the uniform thickness of the second thickness; and the structural property of the second reference flap having the uniform thickness less than the first thickness and greater than the second thickness.

15. A system adapted to provide a flow of breathing gas to the airway of a patient, the system comprising:
  a pressure generating device structured to produce the flow of breathing gas;
  a delivery conduit having a first end coupled to the pressure generating device and an opposite second end, the delivery conduit being structured to receive the flow of breathing gas from the pressure generating device at the first end and communicate the flow of breathing gas from the first end to the second end; and
  a patient interface device having a cushion member coupled to the second end of the delivery conduit, the cushion member being structured to sealingly engage about the airway of the patient and to communicate the flow of breathing gas from the second end of the delivery conduit to the airway of the patient,
wherein the cushion member comprises a sealing flap having a plurality of dimples defined therein,
wherein the sealing flap has a first thickness between the plurality of dimples,
wherein the sealing flap has a second thickness at each dimple that is less than the first thickness, and
wherein the plurality of dimples are arranged in a pattern such that the sealing flap has one or both of:
  a stretch property of a first reference flap having a uniform thickness of the second thickness; and/or
  a structural property of a second reference flap having a uniform thickness less than the first thickness and greater than the second thickness.

16. The system of claim 15, wherein the sealing flap of the cushion member comprises:
  an outer surface structured to sealingly engage the patient at or about the airway of the patient, and
  an inner surface disposed on an opposite side of the sealing flap from the outer surface, and wherein the plurality of dimples are defined in the inner surface.

17. The system of claim 15, wherein the sealing flap has both of: the stretch property of the first reference flap having the uniform thickness of the second thickness; and the structural property of the second reference flap having the uniform thickness less than the first thickness and greater than the second thickness.

* * * * *